US007323583B2

United States Patent
Barr et al.

(10) Patent No.: US 7,323,583 B2
(45) Date of Patent: Jan. 29, 2008

(54) CATALYSTS FOR THE PRODUCTION OF METHYLCHLOROSILANES USING ZINC OXIDE PROMOTERS

(75) Inventors: Mark Kromer Barr, Cary, NC (US); Thomas Matthew Murphy, Apex, NC (US); Michael Glenn Williams, Raleigh, NC (US)

(73) Assignee: SCM Metal Products, Inc., Research Triangle Park, NC (US)

( * ) Notice: Subject to any disclaimer, the term of this patent is extended or adjusted under 35 U.S.C. 154(b) by 0 days.

(21) Appl. No.: 11/083,893

(22) Filed: Mar. 17, 2005

(65) Prior Publication Data

US 2005/0176981 A1   Aug. 11, 2005

Related U.S. Application Data

(62) Division of application No. 10/877,708, filed on Jun. 25, 2004.

(60) Provisional application No. 60/482,664, filed on Jun. 26, 2003.

(51) Int. Cl.
  C07F 7/00 (2006.01)
  B01J 27/06 (2006.01)
  B01J 23/02 (2006.01)
  B01J 53/56 (2006.01)
  B01D 53/50 (2006.01)

(52) U.S. Cl. ............ 556/472; 502/224; 502/343; 502/345; 423/240 R; 423/341; 423/342

(58) Field of Classification Search ........ 502/224, 502/343, 345; 423/240 R, 341, 342; 556/472
See application file for complete search history.

(56) References Cited

U.S. PATENT DOCUMENTS

| | | | |
|---|---|---|---|
| 3,927,121 A | 12/1975 | Grane et al. | |
| 4,504,596 A * | 3/1985 | Schoepe et al. | 502/225 |
| 4,520,130 A | 5/1985 | Hashiguchi et al. | |
| 4,547,482 A | 10/1985 | Osugi et al. | |
| 4,666,945 A | 5/1987 | Osugi et al. | |
| 4,863,894 A | 9/1989 | Chinchen et al. | |
| 4,962,220 A * | 10/1990 | Halm et al. | 556/473 |
| 4,966,986 A * | 10/1990 | Halm et al. | 556/473 |
| 4,996,181 A | 2/1991 | Denny et al. | |
| 5,512,662 A * | 4/1996 | Kalchauer et al. | 556/472 |
| 5,691,268 A | 11/1997 | Koveal et al. | |
| 5,853,681 A | 12/1998 | Denny et al. | |
| 5,990,040 A | 11/1999 | Hu et al. | |
| 6,069,266 A * | 5/2000 | Kalchauer et al. | 556/473 |
| 6,080,699 A | 6/2000 | Pohl et al. | |
| 6,395,244 B1 | 5/2002 | Hartweg et al. | |

OTHER PUBLICATIONS

PCT International Search Report, PCT/US2004/020462, Mar. 27, 2005.

* cited by examiner

*Primary Examiner*—Cam N. Nguyen
(74) *Attorney, Agent, or Firm*—Kalow & Springut LLP; Scott D. Locke, Esq.

(57) ABSTRACT

The present invention provides a catalyst that may be used to facilitate the formation of dimethylchlorosilanes. A catalyst in which copper oxide and zinc oxide are in intimate contact and form agglomerated particles allows for the increased selectively of the production of dimethylchlorosilanes.

12 Claims, 4 Drawing Sheets

CATALYSTS FOR THE PRODUCTION OF METHYLCHLOROSILANES USING ZINC OXIDE PROMOTERS

CROSS REFERENCE TO RELATED APPLICATION

This application claims the benefit of the filing dates of U.S. patent application Ser. No. 10/877,708 filed Jun. 25, 2004 and U.S. Provisional Patent Application Ser. No. 60/482,664, filed Jun. 26, 2003, the entire disclosures of which are hereby incorporated by reference into the present disclosure.

FIELD OF THE INVENTION

The present invention relates to the field of catalysts for use in the production of methylchlorosilanes.

BACKGROUND OF THE INVENTION

Methylchlorosilanes are well known for their many uses, including as raw materials in the production of polysiloxanes and other materials that may be used in applications such as the coating of titanium dioxide, which may, for example, be incorporated into materials such a plastics. One particularly useful methylchlorosilane is dimethyldichlorosilane, which is used in many industrial processes, including the preparation of oils and gums. These materials are, for example, useful starting materials in the manufacture of silicones.

Processes for producing methylchlorosilanes are well known to persons skilled in the art. For example, as described in the background of U.S. Pat. No. 4,645,851, according to the "direct synthesis" or "Rochow synthesis" processes, methylchlorosilanes may be produced directly by reacting methyl chloride with solid silicon in the presence of a copper catalyst.

The reaction for producing dimethyldichlorosilanes is summarized in Formula I below:

$$2CH_3Cl + Si \rightarrow (CH_3)_2SiCl_2 \quad \text{Formula I}$$

However, in most industrial processes, the reaction of methyl chloride with silicon will also produce $(CH_3)SiCl_3$, $(CH_3)_3SiCl$, $CH_3HSiCl_2$, $(CH_3)_2HSiCl$, and other molecular species.

As noted above, in the formation of methylchlorosilanes, one may use copper as a catalyst. One may also use other substances such as zinc, zinc halides, aluminium, tin, manganese, nickel, silver, cobalt, and potassium chloride to promote the formation of methylchlorosilanes.

Zinc has proven to be a particularly useful promoter of the formation of methylchlorosilanes when it is used in combination with copper. However, although zinc is an effective promoter, its use suffers from a number of drawbacks.

First, it is often difficult to provide a consistent level of zinc. This reduces the operability of the system. Second, known processes often suffer from exotherm induced temperature spikes. Third, in these processes there is often instability of the reaction temperature. Fourth, most processes that use zinc inject it in the presence of an inert gas, such as nitrogen, which dilutes the methyl chloride reactant. Fifth, a separate means for adding the zinc is necessary, which adds to the cost of the process. Sixth, known catalysts using zinc have undesirable fluidization properties. Seventh, these catalysts have undesirably low levels of selectivity to the dimethyldichlorosilane. Eighth, as the reaction proceeds, it is difficult to retain the desired level of selectivity. Ninth, the addition of zinc in certain forms may pose safety problems, because metallic zinc and certain other zinc compounds can react with methyl chloride and copper oxide to cause very exothermic reactions.

Thus, there remains a need to develop better ways to optimize the formation of dimethyldichlorosilane. The present invention provides one solution by allowing for the improvement in the selectivity of the formation of dimethyldichlorosilane and through the making of a catalyst in which copper oxide and zinc oxide are in intimate contact in an agglomerated particle.

SUMMARY OF THE INVENTION

The present invention is directed to a catalyst for manufacturing methylchlorosilanes, a process for making the catalyst and a method for using the catalyst. The catalyst is prepared in a manner such that zinc oxide is dispersed throughout a copper oxide material and agglomerated to the copper oxide particles of that material. By dispersing the zinc promoter in the copper oxide material, the zinc promoter can be released in a reactor in a continuous controlled manner as the copper oxide disperses onto the silicon feed.

Accordingly, in one embodiment, the present invention is directed to a catalyst comprised of agglomerated particles, wherein said agglomerated particles are comprised of zinc oxide and copper oxide. This catalyst may be used to facilitate the generation of dimethyldichlorosilane.

In a second embodiment, the present invention is directed to a process for making a catalyst comprised of agglomerated particles, said process comprising agglomerating zinc oxide and copper oxide to form agglomerated particles. This preparation method assists in diminishing the loss of zinc from the reactor by elutriation.

In a third embodiment, the present invention is directed to another process for making a catalyst. This process comprises the steps of: (a) oxidizing and milling water atomized copper shot to form oxidized and milled water atomized shot; (b) co-mixing and blending the oxidized and milled water atomized shot with zinc oxide powder to form a co-mixed and blended product; (c) oxidizing the co-mixed and blended product to create agglomerated particles, wherein said agglomerated particles contain an intimately mixed zinc-oxide phase and copper oxide phase; and (d) milling said agglomerated particles with metallic copper to make a catalyst.

The present invention provides for improvements in the formation of dimethyldichlorosilane. According to the present invention there may be increased dimethyldichlorosilane selectivity at the expense of residue selectivity. This minimizes the problem of known processes for making dimethylchlorosilanes in which after distillation, residue containing materials such as disilanes are generated, and these materials compete for the catalyst. Thus, the catalysts of the present invention reduce selectivity to disilane products. Additionally, when these catalysts are formed by thermally agglomerating the zinc oxide and the copper oxide, then high energy milling the product with elemental copper, the catalysts maintain the higher selectivity to dimethyldichlorosilane while utilizing the silicon more efficiently.

For a better understanding of the present invention, together with other and further embodiments, reference is

DETAILED DESCRIPTION

Figure 1A:
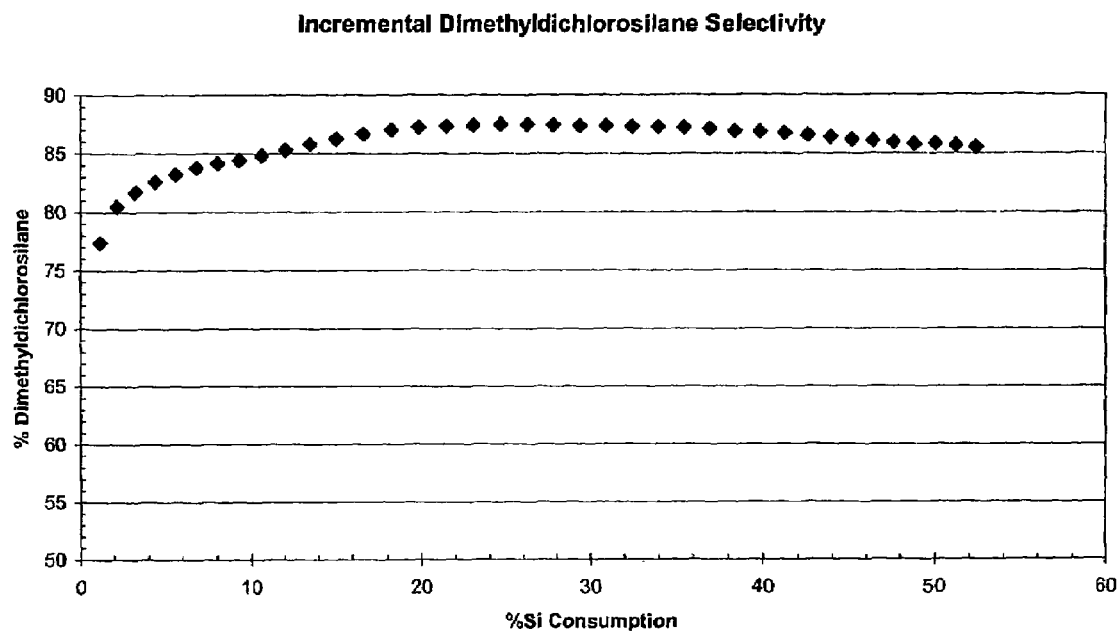
FIGS. 1A and 1B are representations of the incremental dimethyldichlorosilane selectivity and incremental residue selectivity versus the percentage of silicon consumed under the conditions of example 1.

The present invention is directed to improving the production of methylchlorosilanes. By using the catalysts and methods for generating the catalysts described herein, one is able to produce methylchlorosilanes more efficiently than one could produce them according to known methods.

The present disclosure is not intended to be a treatise on either catalysts or the production of methylchlorosilanes. Readers are referred to appropriate available texts and other materials in the field for additional and detailed background information relating to any aspect of practicing this invention.

According to one embodiment, the present invention provides a catalyst comprised of agglomerated particles, wherein said agglomerated particles are comprised of zinc oxide and copper oxide. Preferably, said agglomerated particles are of a size less than 20 microns and have a surface area between 0.5 and 8 m$^2$/g. The phrase "agglomerated particles" as used in the present application refers to particles that although not covalently bound to each other, retain association due to intermolecular forces similar to interlocked particles in a partially sintered ceramic.

The zinc oxide that is used according to the present invention may be generated by any method now known or that comes to be known to persons skilled in the art and that would be appreciated as being useful in connection with the present invention. Alternatively, it may be obtained from commercial vendors such as U.S. Zinc or Zinc Corporation of America.

The phrase "copper oxide" as used in the present application refers copper containing moieties that are comprised of cupric oxide and/or cuprous oxide. Preferably the copper oxide used in the present invention will contain both cupric oxide and cuprous oxide. The copper oxide that is used according to the present invention may be generated by any method now known or that comes to be known to persons skilled in the art and that from reading this disclosure would be appreciated as being useful in connection with the present invention.

The catalyst of the present invention will also preferably contain elemental copper. The elemental copper may be generated by any method that is now known or that comes to be known to persons skilled in the art and that from reading this disclosure would be appreciated as being useful in connection with the present invention, or it may be obtained from commercial vendors. The elemental copper is highly dispersed throughout the surface of the agglomerated particles and may become associated with the agglomerated particles by, for example, being pressed into those particles and held by mechanical forces. For example, by using high energy milling, one may apply a thin layer of copper over the particles.

Collectively, the copper from the elemental copper, the cupric oxide and the cuprous oxide are referred to as the "total copper content." Preferably, the ratio of zinc oxide to the total copper content of the catalyst by weight is between 0.01:1 and 0.65:1. More preferable ranges will readily be determinable by persons skilled in the art based on the applications in which the catalysts will be used.

For example, when in a given system there is to be only a single delivery of copper and zinc, the ratio of zinc oxide to the total copper content of the catalyst by weight is more preferably between 0.01:1 and 0.25:1; and most preferably between 0.01:1 and 0.12:1. However, if one were to use the catalyst of the present invention in a dual feed system, then the ratio of zinc oxide to the total copper content of the catalyst by weight is more preferably between 0.40:1 and 0.65:1.

A methylchlorosilane manufacturer may choose to take advantage of this invention by using the catalyst in at least three different modes depending on the reactor configuration and on the level of sophistication of the manufacturer's process. According to a first mode, the manufacturer could pre-blend the silicon and agglomerated ZnO—Cu$_x$O catalyst together, inject this powder mixture into the reactor and begin to heat it under a methyl chloride flow to fluidize the bed and to initiate the reaction. This mode of operation is a batch mode.

A second possible mode of operation is to fluidize silicon in the reactor and continuously add fresh agglomerated ZnO—Cu$_x$O catalyst package to the fluidize silicon and also continuously add fresh silicon to the fluidized bed. This mode of operation would allow the manufacturer to operate its methylchlorosilanes reactor essentially continuously. For this mode of operation, the lower zinc oxide to copper ratio would be desirable.

A third mode of operation would be for the methylchlorosilanes manufacturer to operate in a manner similar to the second mode of operation suggested, using a low zinc oxide to copper ratio catalyst or primarily a no zinc oxide catalyst, but using a high zinc oxide to copper ratio catalyst on an infrequent basis to raise the zinc level in the fluidized bed in a controlled gentle manner without raising the copper level in the bed excessively. This is sometimes necessary because excessive copper build up in the bed can become a poison to the process for production of methylchlorosilanes.

Under a single delivery system, one may, for example, inject zinc metal, zinc compounds, or zinc oxide at long intervals, for example, approximately every hour, but inject the copper oxide more frequently, for example, every five to ten minutes. Preferably, this injection pattern would be through the use of separate feeds and the zinc species would be injected under an inert gas such as nitrogen.

As noted above, the preferred amount of copper oxide, as well as the amount of the zinc oxide and elemental copper, will depend on the application in which the catalyst will be used. However, preferably: (a) the cuprous oxide is present in an amount between 30 and 95 wt. % based on the weight of the catalyst; (b) the cupric oxide is present in an amount between 2 and 45 wt. % based on the weight of the catalyst;

(c) the elemental copper is present in an amount less than or equal to 25 wt. % based on the weight of the catalyst; and (d) the zinc oxide is present in an amount less than or equal to 18 wt. % based on the ratio of zinc oxide to the total copper content of the catalyst.

When generating a high cupric oxide catalyst, preferably: (a) the cuprous oxide is present in an amount between 75 and 95 wt. % based on the weight of the catalyst; (b) the cupric oxide is present in an amount between 2 and 10 wt. % based on the weight of the catalyst; (c) the elemental copper is present in an amount equal to 2-15 wt. % based on the weight of the catalyst; and (d) the zinc oxide is present in an amount less than or equal to 10 wt. % based on the ratio of zinc oxide to the total copper content of the catalyst.

When generating a high cuprous oxide catalyst, preferably: (a) the cuprous oxide is present in an amount between 30 and 75 wt. % based on the weight of the catalyst; (b) the cupric oxide is present in an amount between 10 and 45 wt. % based on the weight of the catalyst; (c) the elemental copper is present in an amount equal to 4-25 wt. % based on the weight of the catalyst; and (d) the zinc oxide is present in an amount less than or equal to 10 wt. % based on the ratio of zinc oxide to the total copper content of the catalyst.

As persons skilled in the art are aware, one gets higher selectively with higher cupric content, but the reaction rate is lower. Thus, the decision of into which application the catalyst will be used, will determine the preferable amounts of cuprous and cupric oxide. Accordingly, a manufacturer would use a high cuprous content catalyst to increase catalyst activity to produce methylchlorosilanes at a higher rate. Further, a manufacturer would use a high cupric content catalyst to improve selectivity to dimethyldichlorosilane, having a lower activity and a longer reaction induction time.

Under a second embodiment, the present invention provides a process for making a catalyst comprised of agglomerated particles, said process comprising agglomerating zinc oxide and copper oxide to form agglomerated particles.

Preferably the agglomerating is accomplished by the addition of heat. The addition of heat permits the zinc oxide and copper oxide to form the desired association with each other. This addition of heat is preferably performed in the presence of air, which enables the oxidation of the components.

To the agglomerated particles, one may add elemental copper. Preferably the elemental copper is mixed with the agglomerated particles under conditions sufficient to disperse the elemental copper throughout those particles. For example, it may be added under conditions of high energy milling.

Optionally, one may also add tin during the same step that elemental copper is added. Functionally, the tin acts as a co-catalyst with the copper. The tin will preferably be dispersed among the agglomerated particles in the same way that the elemental copper is dispersed. Under this subembodiment, the tin and elemental copper may be added through separate feeds, or they may first be combined with each other and then with the agglomerated particles. Preferably, 200-3000 ppm, more preferably 400-1600 ppm, and most preferably 800-1200 ppm weight of tin relative to the weight of copper is used in the contact mass.

Under one particularly preferred embodiment, the present invention provides a process for making a catalyst, said process comprising the steps of: (a) oxidizing and milling water atomized copper shot to form oxidized and milled water atomized shot; (b) co-mixing and blending the oxidized and milled water atomized shot with zinc oxide powder to form a co-mixed and blended product; (c) oxidizing the co-mixed and blended product to create agglomerated particles, wherein said agglomerated particles contain an intimately mixed zinc-oxide phase and copper oxide phase; and (d) milling said agglomerated particles with metallic copper to make a catalyst.

Thus, according to this process, water atomized copper shot, which as persons skilled in the art know contains elemental copper, cuprous oxide and copper oxide, is oxidized and milled to an appropriate particle size distribution. This material is co-mixed and thoroughly blended with zinc oxide powder. The co-mixed material may be further oxidized in order to increase the copper oxide content and to create particles that contain intimately mixed zinc oxide-copper oxide phases thereby forming agglomerated particles of zinc oxide and copper oxide. The agglomerated particles are then milled with metallic copper in order to form the desired particle size distribution.

As with the embodiment above, in this embodiment, one can also optionally mill the agglomerated particles with tin. Thus, the tin may be milled into the copper oxide at the same high-energy mill at which the elemental copper is added. The milling of the tin allows for the tin to be evenly distributed while remaining in its metallic form. By milling the tin, one is able to avoid making tin-oxide.

The above-described catalysts and catalysts produced by the above-described processes are particularly useful in generating dimethyldichlorosilanes from silicon and methyl chloride. The catalysts may be added to systems or reactors that contain methylchlorosilanes in a feed that contains methylchloride. This is in contrast to systems that add metallic zinc separately form the copper oxides. In those systems, the zinc is typically added through a feed that contains an inert gas, e.g., nitrogen gas.

By injecting the catalyst into the system or reactor in the presence of methyl chloride gas, one is able to minimize gas dilution, which allows for a more efficient process.

Further, because the catalysts of the present invention contain both the copper oxide catalyst and the zinc oxide promoter, one does not need to construct separate feed valves for each of these materials.

Still further, there are benefits to using the zinc oxide and not zinc metal. For example, costly maintenance of the feed valve equipment can be avoided. Additionally, the zinc oxide-copper oxide particle allows the zinc promoter to be added with the copper oxide in a more continuous manner than occurs in traditional methods. This permits one to avoid some of the temperature spikes that can be generated from independent injection of metallic zinc to a reactor.

EXAMPLES

The present invention is illustrated by the following examples. These are merely illustrative and should not be construed as limiting the scope of the invention.

Reaction Test Equipment and Chemical Reactants

In connection with the examples below, reaction tests were conducted in a stirred bed reactor. The reactor is constructed of low carbon stainless steel, 28 inches high and 2 inches internal diameter. The reactor and reaction mass is heated by a fluidized bed sand bath and the contact mass is continuously stirred to insure uniform temperature throughout the contact mass and homogeneous contact between the contact mass and methyl chloride.

The reaction conditions for all of these examples were: 100.00 grams ground silicon, 120 sccm $CH_3Cl$ gas, and a reaction temperature of 300° C. The catalyst and appropriate additives (tin, zinc, zinc oxide, as appropriate) were admixed with the silicon before addition to the reactor. The crude product composition was measured using a Hewlett-Packard gas chromatograph (Model 5890-II with a TCD detector) equipped with a 30% OV-210 Chromosorb PAW-DMCS 80/100 12 ft.×⅛' stainless steel column. The reaction rate and crude production activity is determined by using 3.00 sccm nitrogen gas as an inert marker gas mixed into the methyl chloride gas feed stream. Mass flow controllers on the methyl chloride gas and on the nitrogen gas insure a uniform and constant flow rate for both gases.

All reactions tests used commercially available chemical grade silicon purchased from Elkem Metals Company, Alloy, W. Va. The silicon was ball milled and blended to provide a uniform and consistent silicon feed. The major impurities, as provided by the manufacturer and confirmed by an outside testing laboratory, are 0.32% Fe, 0.14% Al, and 0.004% Ca. The particle size distribution of the test silicon is shown in Table I below.

TABLE 1

Silicon particle size distribution

| % (wt/wt) | Size (μm) |
|---|---|
| 10 | 116 |
| 25 | 97 |
| 50 | 70 |
| 75 | 32 |
| 90 | 5.9 |

All tests used commercially available materials. The "High Purity Grade" methyl chloride was obtained from Air Products, Inc. The zinc oxide used was Kadox 911, purchased from Zinc Corporation of America, Monaca, Pa. The zinc powder was purchased from the New Jersey Zinc Company, Palmeton, Pa. The tin powder used was manufactured by SCM Metal Products, Research Triangle Park, N.C.).

General Catalyst Preparation Method

In a continuous process two materials were manufactured for use as raw materials for these methylchlorosilanes catalysts.

The first raw material preparation is related to the present invention. To prepare the ZnO-copper oxide material, 81.0 lbs. of an approximately 95% cuprous oxide powder with a typical $d_{50}$ particle size of approximately 15 μm was thoroughly mixed with 10.0 lbs. zinc oxide with a $d_{50}$ particle size approximately 0.12 μm. The mixing was accomplished by roll blending the two components together until the physical mixture appeared uniform. The thoroughly mixed powders were oxidized on a thin layer belt furnace at 900-1000° F. with a residence time of approximately 30 minutes to produce an agglomerated ZnO-copper oxide particulate material. This material was further processed to make an active and selective catalyst as described below.

For the second raw material, the mixed copper oxide material manufactured immediately before that which was mixed with the ZnO was also collected and oxidized on a thin layer belt furnace at 900-1000° F. with a residence time of approximately 30 minutes to produce a mixed copper oxide particulate material. The composition was approximately 50% cuprous oxide, 45% cupric oxide, and 5% free copper. This mixed copper oxide material was used as the basis for comparison to the ZnO-copper oxide material described above.

Example 1

The standard catalyst preparation is not an embodiment of the present invention, but is used for comparison to the catalyst preparations of the present invention. The preparation of the catalyst and the use of this type of catalyst are well known to those skilled in methylchlorosilanes catalysis.

A 300.00 g hammer milled air oxidized mixed oxidation state copper powder (manufactured as described above) and 30.00 g of −325 mesh high surface area copper powder were charged to a Pilamec Megaport® Vibration mill loaded with 3000 g ³⁄₁₆" low carbon steel milling medium. The materials were comminuted for 4.0 hour, removed from the mill and separated from the milling medium, reloaded into the mill and comminuted an additional 4.0 hour for a total milling time of 8.0 hour. The output from the mill was an active and selective catalyst for the reaction of methyl chloride with silicon powder to produce dimethyldichlorosilane.

The catalyst was tested as described above. Silicon powder (100.00 g), the catalyst (3.00 g), zinc powder (0.257 g), and tin powder (0.0030 g) were admixed together and added to the stirred bed reactor under a methyl chloride gas flow. A gas chromatographic analysis of the gases coming from the reactor was taken after the contact mass was added to the reactor as the reactor was heated to 300° C. Gas chromatographic analysis data were collected every hour throughout the duration of the reaction.

Figure 1B:
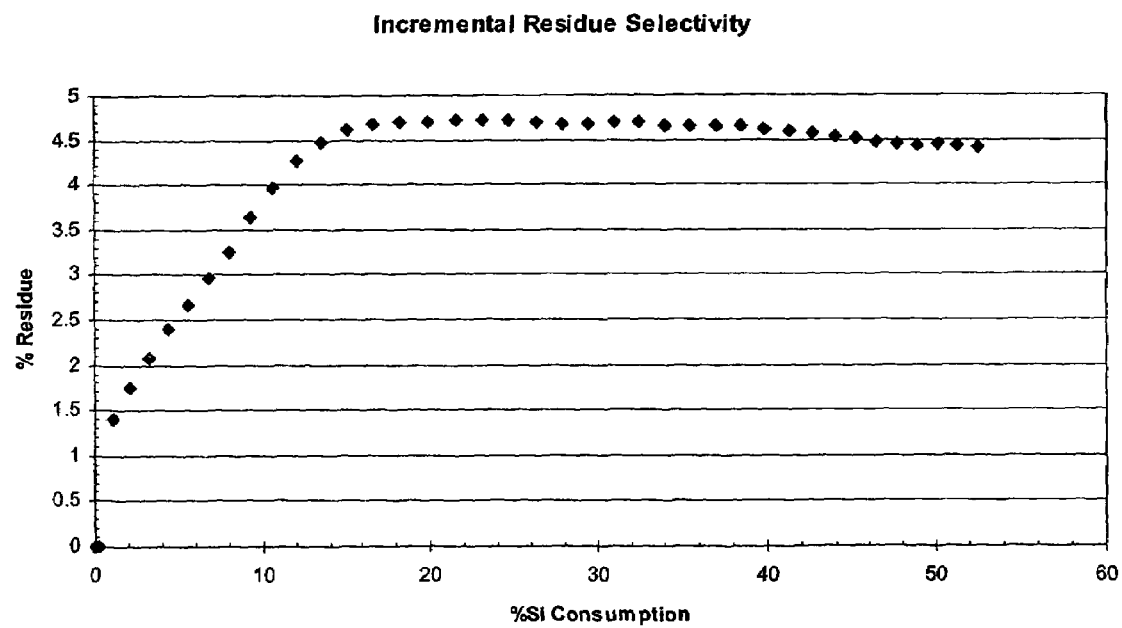

FIGS. 1A and 1B show the selectivity of dimethyldichlorosilane and residue versus the percentage of silicon consumed during the reaction.

This example shows the preparation of an active and selective catalyst with existing technology that is well known to those skilled in the art of methylchlorosilanes catalyst preparation. This example also shows the use and performance of the catalyst by those knowledgeable in methylchlorosilanes direct synthesis reactions. This is a baseline standard catalyst synthesis and reactor test.

Example 2

The catalysts prepared for this invention used the ZnO-copper oxide material described earlier.

The ZnO-copper oxide material (300.00 g) was blended with 26.83 g approximately 98%-325 mesh copper metal and loaded into a Pilamec Megaport® Vibration mill loaded with 3000 g ³⁄₁₆" low carbon steel milling medium. The contents of the mill were comminuted for 4.0 hours, separated from the milling medium and repositioned in the mill for an additional 4.0 hours. The finished product was removed from the mill and stored until use.

Figure 2A:
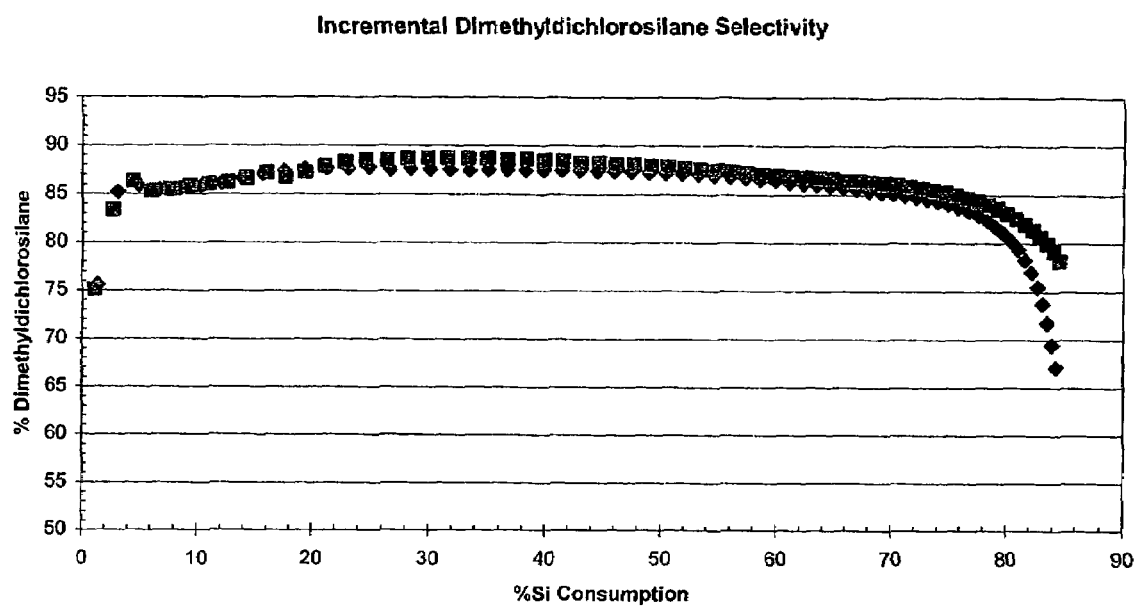
FIGS. 2A and 2B are representations of the incremental dimethyldichlorosilane selectivity and incremental residue selectivity versus the percentage of silicon consumed under the conditions of examples 2.
Figure 2B:
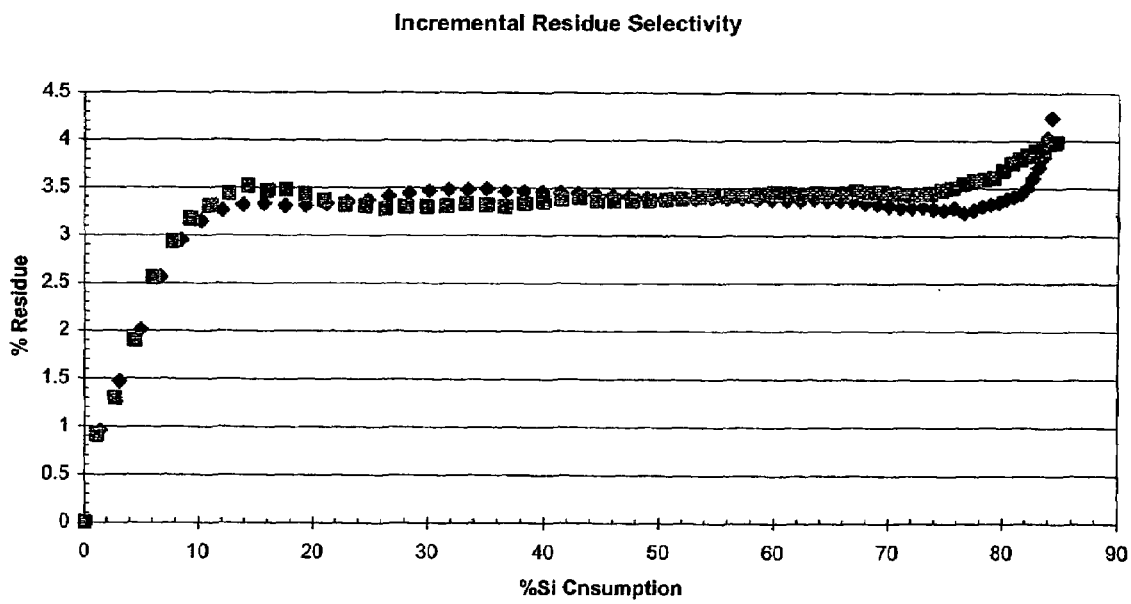

The reactor test was the same as that followed for the standard catalyst test described previously. The contact mass for two reaction tests shown below was composed of 100.00 g silicon, 3.34 g ZnO-copper oxide catalyst prepared as described above, and 0.0030 g tin. The incremental dimethyldichlorosilane selectivity and incremental residue selectivity versus the percentage of silicon consumed are shown in FIGS. 2A and 2B.

These examples demonstrate the technology disclosed in this patent application for the preparation of an improved methylchlorosilanes catalyst. The reaction conditions and use of the catalysts are well known to those skilled in methylchlorosilanes catalysis, but the dimethyldichlorosilane selectivity is increased and the residue selectivity is decreased because of the catalyst preparation technology disclosed in this application.

Example 3

In another embodiment of this invention, the ZnO-copper oxide material prepared above (300.00 g) was blended with 26.83 g approximately 98%-325 mesh copper metal, and 0.235 g tin powder. This powder mixture was loaded into a Pilamec Megaport® Vibration mill loaded with 3000 g $\frac{3}{16}$" low carbon steel milling medium. The contents of the mill were comminuted for 4.0 hr, separated from the milling medium and repositioned in the mill for an additional 4.0 hr. The finished product was removed from the mill and stored until use.

Figure 3A:
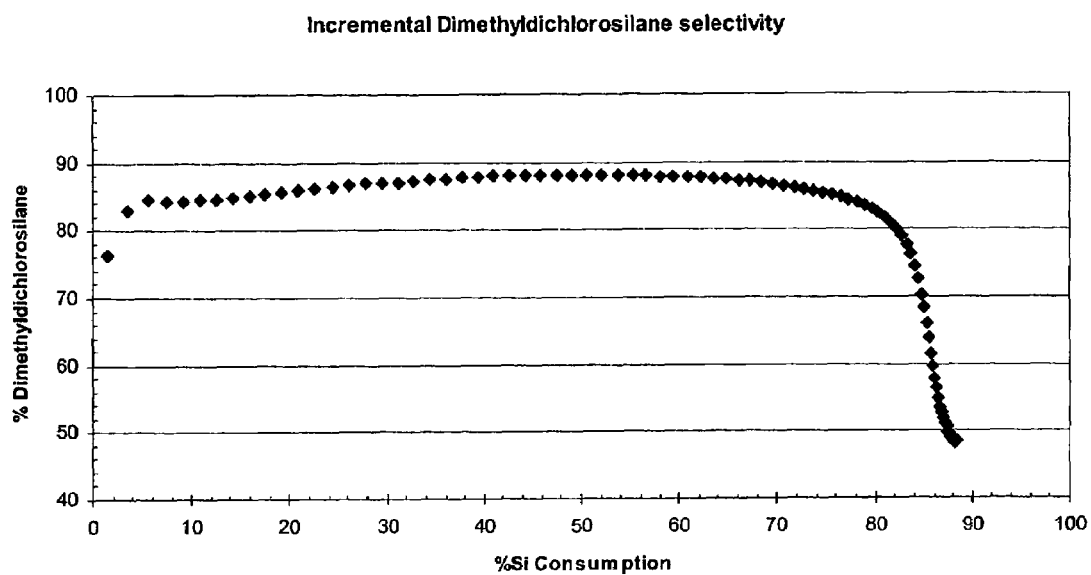
FIGS. 3A and 3B are representations of the incremental dimethyldichlorosilane selectivity and incremental residue selectivity versus the percentage of silicon consumed under the conditions of example 3.
Figure 3B:
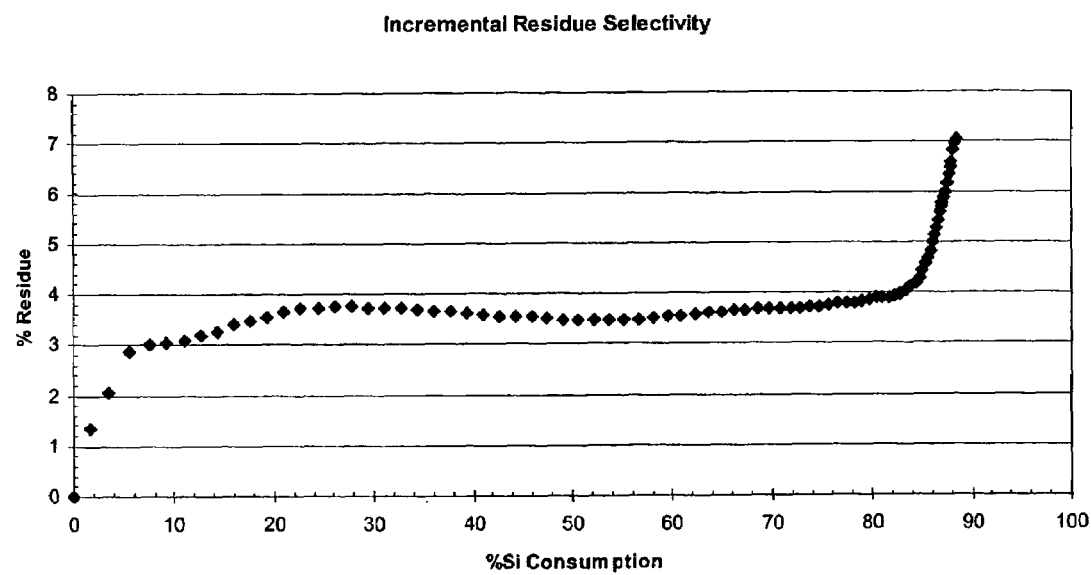

The catalysts prepared by this process were active and selective. The addition of tin to the ZnO-copper oxide catalyst particle is a convenient means of introducing tin into a methylchlorosilanes reaction. The catalysts were tested in a manner similar to the standard catalyst test procedure. The silicon powder (100.00 g) and 3.34 g of the catalyst were mixed and added to the reactor as described previously. The incremental dimethyldichlorosilane and incremental residue selectivity for the reaction catalyzed with this catalyst are shown in the graphs of FIGS. 3A and 3B.

This example shows that the disclosed catalyst preparation technology is effective when applied to catalysts that contain tin. The reactor test conditions are well known to those knowledgeable in methylchlorosilanes direct synthesis reactions.

Example 4

In another catalyst preparation not covered by this patent, but used for comparison purposes, the mixed copper oxide material prepared above (300.00 g) was blended with 30.00 g approximately 98%-325 mesh copper metal, and 35.41 g Kadox 911 Zinc Oxide, and loaded into a Pilamec Megaport® Vibration mill loaded with 3000 g $\frac{3}{16}$" low carbon steel milling medium. The contents of the mill were comminuted for 4.0 hr, separated from the milling medium and repositioned in the mill for an additional 4.0 hr. The finished product was removed from the mill and stored until use.

Figure 4A:
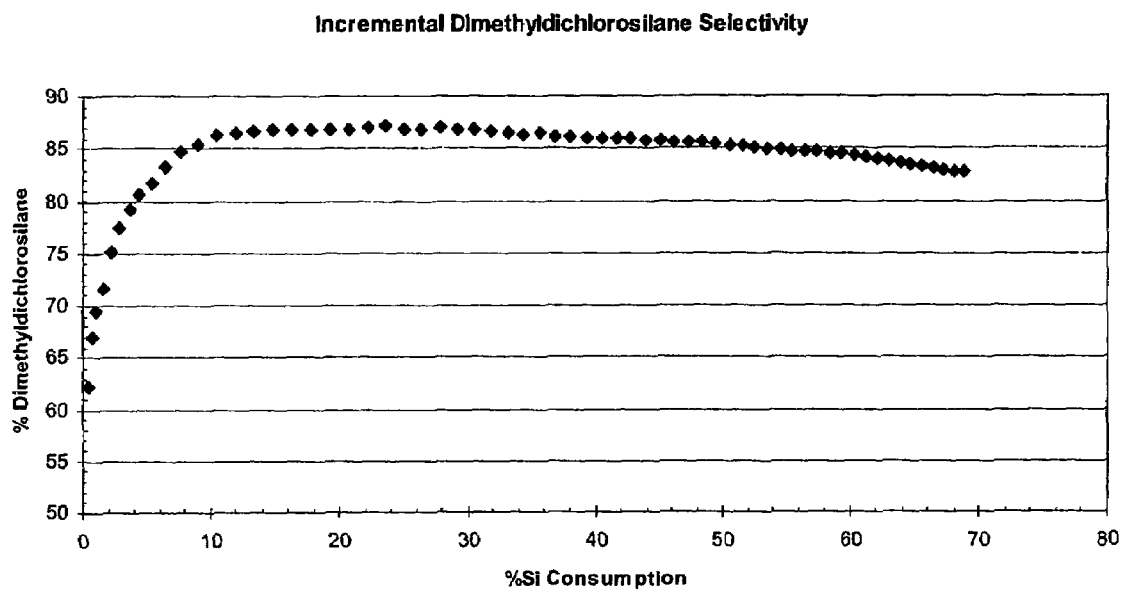
FIGS. 4A and 4B are representations of the incremental dimethyldichlorosilane selectivity and incremental residue selectivity versus the percentage of silicon consumed under the conditions of example 4.
Figure 4B:
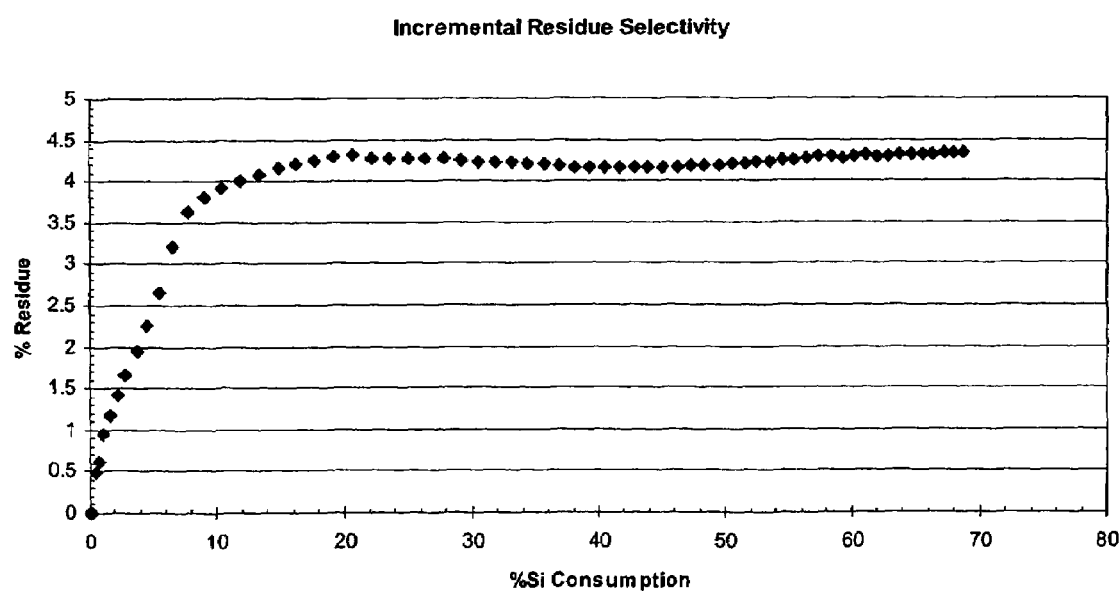

The reactor test was the same as that followed for the standard catalyst test described previously. The contact mass for the test was composed of 100.00 g silicon, 3.00 g standard copper oxide catalyst described above, 0.30 g ZnO (Kadox 911), and 0.030 g tin powder. The incremental dimethyldichlorosilane selectivity and incremental residue selectivity versus the percentage of silicon consumed are shown in FIGS. 4A and 4B.

Mixed oxidation state copper oxide catalyst was made from mixed oxidation state copper oxide with an approximate composition 5% free copper, 50% cuprous oxide, and 45% cupric oxide. A 300.00 g aliquot of the mixed copper oxide was admixed with 30.00 g copper powder, blended and loaded into a Pilamec Megaport® Vibration mill loaded with 3000 g $\frac{3}{16}$" low carbon steel milling medium. The contents of the mill were comminuted for 4.0 hr, separated from the milling medium and repositioned in the mill for an additional 4.0 hr. The finished product was removed from the mill and stored until use.

This example demonstrates that although ZnO comminuted with mixed copper oxides is an effective promoter of the methylchlorosilanes catalyst package, it is not as effective a technology as that disclosed in this patent application. The comminuted ZnO promoter is less selective to dimethyldichlorosilane and shows higher selectivity to residue.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A method of making methylchlorosilanes, said method comprising contacting silicon and methylchloride with a catalyst, wherein said catalyst comprises agglomerated particles that are comprised of zinc oxide and copper oxide, wherein said copper oxide comprises cupric oxide and cuprous oxide.

2. The method according to claim 1, wherein said agglomerated particles have a size less than 20 microns and a surface area between 0.5 and 8 $m^2/g$.

3. The method according to claim 1, wherein the catalyst further comprises elemental copper.

4. The method according to claim 1, wherein the ratio of zinc oxide to total copper content of the catalyst by weight is between 0:01:1 and 0.65:1.

5. The method of claim 4, wherein the ratio of zinc oxide to total copper content of the catalyst by weight is between 0.01:1 and 0.12:1.

6. The method according to claim 4, wherein the ratio of zinc oxide to total copper content of the catalyst by weight is between 0.40:1 and 0.65:1.

7. The method according to claim 1 further comprising pre-blending said silicon and agglomerated particles to form a powder mixture, injecting said powder mixture into a reactor and heating the powder mixture under a methyl chloride flow.

8. The method according to claim 1 further comprising fluidizing silicon in a reactor and continuously adding fresh agglomerated catalyst particles and fresh silicon.

9. The method according to claim 1 further comprising injecting a zinc containing compound and copper oxide into separate feeds, wherein the copper oxide is injected more frequently than the zinc containing compound.

10. The method according to claim 1 further comprising adding heat.

11. The method according to claim 1, further comprising introducing tin.

12. The method according to claim 11, wherein the amount of tin is 200-300 ppm relative to the weight of copper.

* * * * *